Jan. 28, 1941. G. L. POLK Plant Pat. 444

LIME TREE

Filed June 4, 1940

INVENTOR
George L. Polk
BY
A. H. Golden
ATTORNEY

Patented Jan. 28, 1941

Plant Pat. 444

UNITED STATES PATENT OFFICE

444

LIME TREE

George L. Polk, Homestead, Fla.

Application June 4, 1940, Serial No. 338,721

1 Claim. (Cl. 47—62)

My discovery relates to a lime tree and its fruit. More particularly, my discovery comprises a novel and distinctive variety of lime tree and its fruit, which originated as the sport of a budded tree of the well known regular Persian lime stock.

Figure 1:
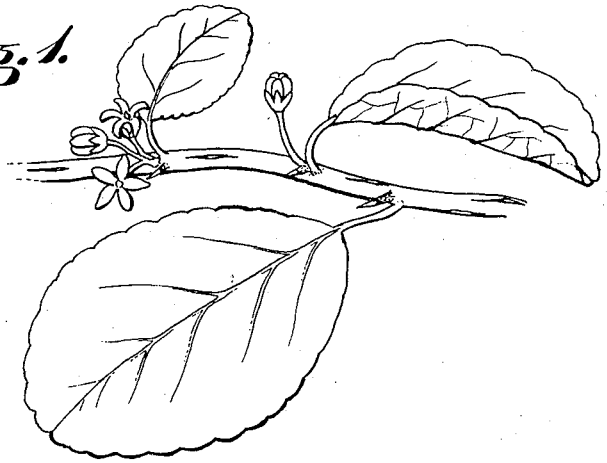
Figure 2:
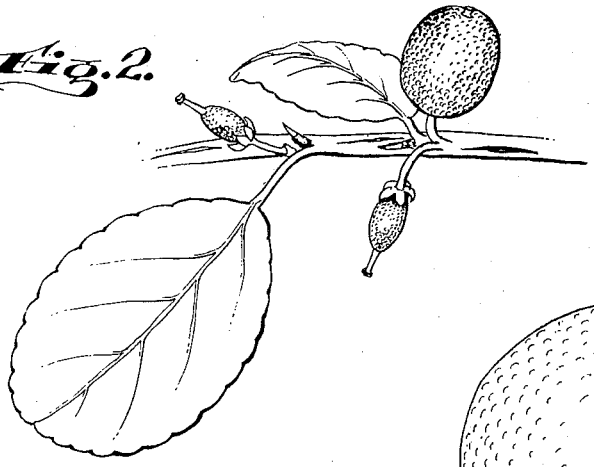
Figure 3:
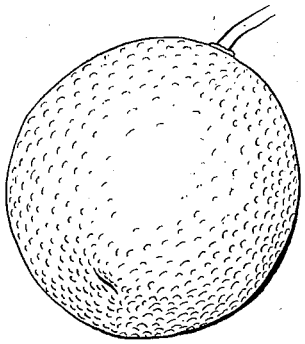
Figure 4:
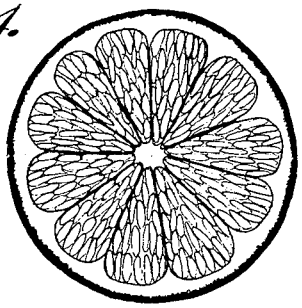

In the accompanying drawing of my lime tree and its fruit, I show in Fig. 1 a piece of bearing wood having three leaves and several of the blossoms. The drawing illustrates quite well the shape of the leaves and the nature of the blossoms. In Fig. 2, I show a small piece of a bearing branch with the fruit in process of growth. Fig. 3 illustrates the shape of the fruit, as well as the feature that my lime does not have a lemon shaped tip on its bud end, there being but the outline of a scar where the bud end would normally be. Fig. 4 shows a section of the fruit of Fig. 3 and illustrates the nature thereof.

The new lime tree is propagated through budding or grafting, and has been budded on root stocks such as rough lemon, grapefruit, Cleopatra and sour orange. In all cases, the tree has constantly retained its identity, and the variety has not played out, as so often happens with supposed discoveries of new varieties.

The tree of my new lime grows somewhat more slowly than does the standard Persian lime tree, and its leaves are much deeper green, are heavier, and somewhat rounded at the tips. The bearing wood is much harder than is the wood of the Persian lime tree, and is decidedly striped, being similar in this respect to the bearing wood of orange trees. Moreover, while in the Persian lime tree the branches are inclined to droop, the branches of my tree grow upright and are inclined to make a much better shaped and more compact tree than the Persian lime.

The fruit of my tree matures somewhat earlier than does the fruit of the Persian lime, and I find my tree considerably more prolific than the Persian lime. The limes produced on my tree are round in shape and there are no lemon shaped tips formed on the bud end, as in the case of the Persian lime. While the fruit is slightly smaller than the fruit of the Persian lime, it has the same general appearance as the Persian lime, and about the same degree of seedlessness. The juice content of my lime fruit is equivalent to that of the Persian lime, except that in the earlier stages of development, it has more juice than the Persian and other limes.

I have found that my tree is very much more resistant to all the fungus diseases that are so fatal to the standard Persian lime. It seem that the fungus does not attack the wood as it does the wood of other lime trees. As a basis of comparison, it may be said that my tree is about as resistant to diseases of the bark as is the round orange tree. To illustrate the nature of my tree and its resistance to fungus, I have in the last few years top-worked over twenty large citrus trees of rough lemon and grapefruit root to my new lime, and they have made magnificent trees, all quite clean of fungus. Other and even larger citrus trees top-worked to Persian limes and under similar conditions, have been badly infected by fungus. In addition, my tree has proven more resistant to dry weather than the Persian lime.

In addtion to the tree being resistant to fungus, the fruit thereof is also much more resistant to fungus than is the fruit of the Persian lime. While in the case of the Persian lime it is well known that the fruit tends to decay on the tree, it does not do so on my tree.

Where originated: Grove of Mrs. Julia Polk, north side of Avocado Drive, East of Krome Avenue, Dade County, Florida.
When originated: Prior to 1934.
How originated: Bud sport of Persian lime tree.
By whom originated: George L. Polk.
When first propagated: October, 1934.
By whom first propagated: George L. Polk.
By whom introduced to the trade: Not yet introduced.
When introduced to the trade: Not yet introduced.
Name and address present owner: George L. Polk, Homestead, Florida.
Where specimens described were grown: Grove of George L. Polk, Homestead, Florida.
Dates first and last picking: June 10–October 1 (estimated).
Tree: Medium, vigorous, spreading, dense, productive, regular bearer.
*Trunk.*—Medium.
*Branches.*—Stocky, much divided, branchlets rounded, spines small and stiff, relatively scarce compared to common Persian lime. Vegetative growth (suckers) slight, vigorous.
*Leaves.*—Thick, leathery, large, dense, dark green uni-foliate, elliptical, bluntly pointed; glands numerous; peticles narrowly winged, distinct from blade-twig.
*Keeping quality.*—Good.
*Shipping quality.*—Good.
*Resistance to*: Insects—medium; diseases—good.

General notes: This plant differs from the ordinary Persian lime, of which it is a bud sport, in the following characteristics: *1. Type of growth*—it makes a considerably more stocky, erect tree, with unusually stout flushes of growth which resist wind damage to a greater degree than do those of the Persian. *2. Fruit*—the fruit is consistently smaller than the Persian lime and develops a satisfactory content of available juice at an earlier stage. The fruit is as a rule quite round, and is distinguished by the flat base and the persistent style, which remains until the fruit is ready to pick, at which time it falls away easily, leaving a slight scar. *3. Resistance to drought*—trees of this lime budded on rootstocks of rough lemon, grapefruit, sour orange and Cleopatra have endured severe droughts with noticeably less wilting and reduction of crop than trees of ordinary Persian lime under the same conditions. *4. Resistance to disease*—the tree is highly resistant to the "lime bark disease" which is commonly found in the ordinary Persian. Attempts to induce the disease by inoculation have consistently failed. *5. Prolificness*—the tree bears larger crops of fruit than Persian limes under the same conditions.

*Flowers.*—Normal period of bloom—late winter, two lesser blooms in late spring and summer; solitary and small terminal cymes.

Fruit:

*Size.*—Uniform: *circumference*—5½–5¾ inches; *axial diam.*—about 1¾ inches; *transverse*—1¾ inches.

*Form.*—Uniform; symmetrical; regular-oblique; globose, slightly obovoid. *Base*—rounded, smooth. *Apex*—scarred, flat. *Navel*—wanting.

*Stem*—*Size*—short, stout; *color*—light-green; *position*—straight.

*Calix.*—Raised; *segments*—number 5, obtuse.

*Rind.*—Adherent to pulp; close. *Surface*—grained. *Flavor*—Aromatic, testing of lime oil; thickness—7/32 to 3/32 inch. *Color*—green; *bloom*—wanting; *oil cells*—inconspicuous, medium, even.

*Segments.*—Number 10; *size*—uniform; cling together; *dorsal surface*—flat; *segment walls*—thin, tender.

*Flesh color.*—Very light green. *Texture*—tender, melting. *Rag in flesh*—little; *vesicles*—long, narrow. Form similar to Persian. *Juice*—abundant, evenly distributed in sections. *Color*—very light green. *Flavor*—acid, rich. *Quality*—best.

*Seeds.*—Wanting.

*Pith.*—Solid; *thickness*—3/32–⅛ inch.

*Season.*—Early compared with common Persian lime.

I claim:

A new and distinct variety of lime tree as described, characterized by its resistance to those fungus diseases which attack lime trees, its prolific bearing habits, and the shape of its fruit.

GEORGE L. POLK.